US006981425B2

(12) United States Patent
Frederick

(10) Patent No.: US 6,981,425 B2
(45) Date of Patent: Jan. 3, 2006

(54) DYNAMIC FORCE MEASURING INSTRUMENT HAVING A FOIL BELT TRANSDUCER

(75) Inventor: Leonard L. Frederick, Whippany, NJ (US)

(73) Assignee: Frederick Engineering, Co., Whippany, NJ (US)

( * ) Notice: Subject to any disclaimer, the term of this patent is extended or adjusted under 35 U.S.C. 154(b) by 78 days.

(21) Appl. No.: 10/435,475

(22) Filed: May 12, 2003

(65) Prior Publication Data

US 2004/0099063 A1 May 27, 2004

Related U.S. Application Data

(60) Provisional application No. 60/428,272, filed on Nov. 22, 2002.

(51) Int. Cl.
*G01L 1/00* (2006.01)

(52) U.S. Cl. .................................................. 73/862.391

(58) Field of Classification Search .................. 73/818, 73/862.381, 862.391, 862.451, 158, 159, 73/160, 12.09

See application file for complete search history.

(56) References Cited

U.S. PATENT DOCUMENTS 4,216,403 A * 8/1980 Krempl et al. .............. 310/328
4,484,061 A * 11/1984 Zelinka et al. .............. 392/480
4,817,625 A * 4/1989 Miles .......................... 600/534
4,822,659 A * 4/1989 Anderson et al. ............. 428/99
5,104,701 A * 4/1992 Cohen et al. .............. 428/34.5
6,543,102 B1 * 4/2003 Zitzmann ..................... 338/25

* cited by examiner

*Primary Examiner*—Max Noori
(74) *Attorney, Agent, or Firm*—Ronald E. Greigg

(57) ABSTRACT

This invention defines improvements in dynamic force measuring instruments, which allow for the acquisition of data, such as depth driven and force applied, from the driven pile with the sensor being designed to make it easier to place the sensor with respect to the pile to be driven. In particular, the invention comprehends the use of a foil sensor, which is covered with insulation. An inductive belt sensor can be wrapped around the pile anytime during the driving of the pile. The signal from the belt sensor in response to stress in the pile from the pile driver is fed to a computer in the same manner as for the coil. The belt consists of a metallic strip of aluminum or copper or other conductive metallic material covered on both sides and ends by insulation material. At one end of the metallic strip an electric cable is connected which leads through a connector to a computer. The metallic strip picks up the magnetostriction signal, which is proportional to the resistance the pile encounters during driving. The signal curves displayed on the computer are identical to those picked up by the wire wound coil.

16 Claims, 2 Drawing Sheets

12
17
16
14
13
11
10
21
22
61
62
19

DYNAMIC FORCE MEASURING INSTRUMENT HAVING A FOIL BELT TRANSDUCER

This application claims the benefit of Provisional Application No. 60/428,272, filed Nov. 22, 2002.

FIELD OF THE INVENTION

This application is for an improvement over U.S. Pat. No. 6,098,447, entitled DYNAMIC FORCE MEASURING INSTRUMENT FOR FOUNDATION AND CASING, issued to LEONARD L. FREDERICK, on Aug. 8, 2000. The improvement allows for the acquisition of data, such as depth driven and force applied, from the driven pile with the sensor being designed to make it easier to place the sensor with respect to the pile to be driven.

BACKGROUND OF THE INVENTION

Reference is made to U.S. Pat. Nos. 3,931,729 and 6,098,447, both of which describe the use of magnetostriction and the Villari effect in measuring the pile resistance while it is being driven, and both of which are incorporated herein by reference. The Villari effect is a phenomenon that when one applies an external stress to a magnetostrictive material, such as iron, a corresponding strain will develop in the material, which strain will in turn induce a magnetic field in the material. The above patents, as well as the present invention, take advantage of this effect by using a force measuring inductive sensor to sense a force applied to a pile by a pile driver. The sensor generates a signal in response to the magnetic field caused by this force, which signal is proportional to the force on the pile.

In both patents a coil of wire was depicted as the sensor. In practice it has been found that this coil was objectionable because it was difficult to thread the coil under the bottom end of the pile or over the top of the pile.

The present invention overcomes this problem. Instead of a coil of wire, it has been discovered that an inductive belt sensor can be wrapped around the pile anytime during the driving of the pile. The signal from the belt sensor in response to stress in the pile from the pile driver is fed to a computer in the same manner as for the coil. The belt consists of a metallic strip of aluminum or copper or other conductive metallic material covered on both sides and ends by insulation material. At one end of the metallic strip an electric cable is connected which leads through a connector to a computer. The metallic strip picks up the magnetostriction signal which is proportional to the resistance the pile encounters during driving. The signal curves displayed on the computer are identical to those picked up by the wire wound coil.

U.S. Pat. No. 4,791,372 to Kirk et al discloses the use of a sensor for sensing the spin echo signals in a magnetic resonance imaging system. The sensor is disclosed as a metal sheet covered with insulation, with the ends on one side of the sheet bearing VELCRO or other hook and loop type fastener means fixed thereto. The sensor is wrapped about a patient in conforming fashion to form a coil with the facing ends of the sensor, bearing VELCRO or other hook and loop type fastener means, overlapping so that the overlapping metal sheet and intervening insulation form a capacitance in parallel with the coil. The coil/capacitance is connected to a capacitive tuning circuit to tune the coil/capacitor toward the resonance of the particular Lamor frequency being sensed.

The belt sensor of the present invention differs from that shown by Kirk et al in that the ends of the metallic foil do not overlap to form a parallel capacitor. The metallic foil of the invention also does not completely encircle the test object as does Kirk et al or conform to the test object as does Kirk et al but is spaced therefrom. Kirk et al's sensor also requires a tuning circuit, since its coil/capacitance must be tuned to resonance. The sensor of the invention is an inductive sensor only and requires no tuning.

Through tests of the foil belt sensor in the field, it has been determined that fifty tons of pile bearing equals one volt on the impact curve developed by the sensor of this invention.

Another method to calibrate the foil transducer is through the use of the dead load test for piles. By this system a pile is driven into the ground with the foil transducer wrapped around the pile in the prescribed manner. The peak voltage is noted on the computer. Then a dead load is applied to the pile until it fails to support the load. This is known as the Ultimate Bearing Capacity. The ultimate bearing capacity will be the peak voltage on the computer. By dividing the total load in tons by the voltage, one can arrive at the number of tons per volt sensed.

OBJECTS OF THE INVENTION

Accordingly, it is the principal object to provide a sensor for a pile driving system which is simpler to mount on the pile being driven, and which can be placed around the pile at any time during the driving of the pile.

It is also an object of this invention to provide a transducer having simplified electric circuitry compared to the state of the prior art, and yet that will still accurately measure the maximum threshold force from the pile driving hammer that can be applied to the pile without causing permanent penetration of the pile into the ground. Thus, the maximum bearing capacity of the pile can be determined immediately and this eliminates the need for a costly dead load bearing test.

It is a still further object of this invention is to provide a circuit that improves pile bearing measurement techniques so that the output of the circuit is compatible with a computer or an oscilloscope.

SUMMARY AND ADVANTAGES OF THE INVENTION

The invention comprehends the use of a foil sensor which is covered with insulation. At any time this sensor can be placed around the pile being driven, and provide electrical indication of the force being applied to the pile. The sensor is a passive foil placed around the pile and does not require physical contact with the pile for measurement.

Further objects and advantages will become more apparent from a reading of the following specification taken in conjunction with the drawings

DESCRIPTION OF THE PREFERRED EMBODIMENT

Figure 1:
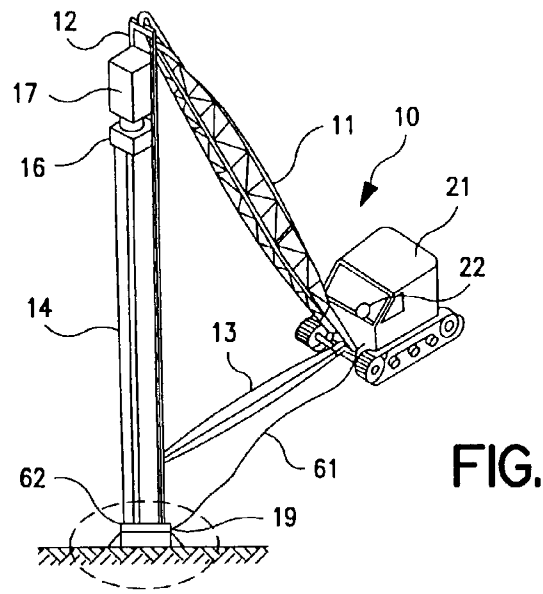
FIG. 1 shows a perspective view of a mobile pile driver mounted on a crane with the relative positions of the transducer and readout units.
Figure 2:
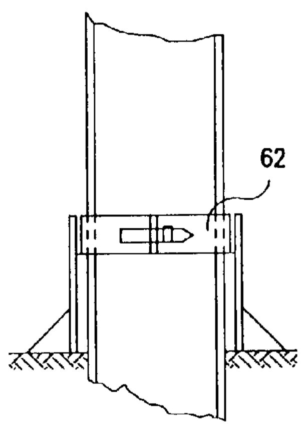
FIG. 2 shows an enlarged view of a portion of FIG. 1, particularly showing the manner in which the foil is placed around the pile.

Turning now to FIG. 1, there is a view of the customary mobile pile driving crane, which has the same details as depicted in U.S. Pat. Nos. 3,931,729 and 6,098,447, except the wire wound transducer has been replaced with a foil belt transducer 62, and dual cable conductor has been replaced by a single conductor cable 61 connected to one end of the foil. It should be noted, however, that although the single conductor cable 61 is preferred because it requires less conductors, clearly a dual conductor cable could just as easily be used with the second conductor connected to the other end of the foil. FIG. 2 shows an enlargement of a section of FIG. 1.

Figure 3:
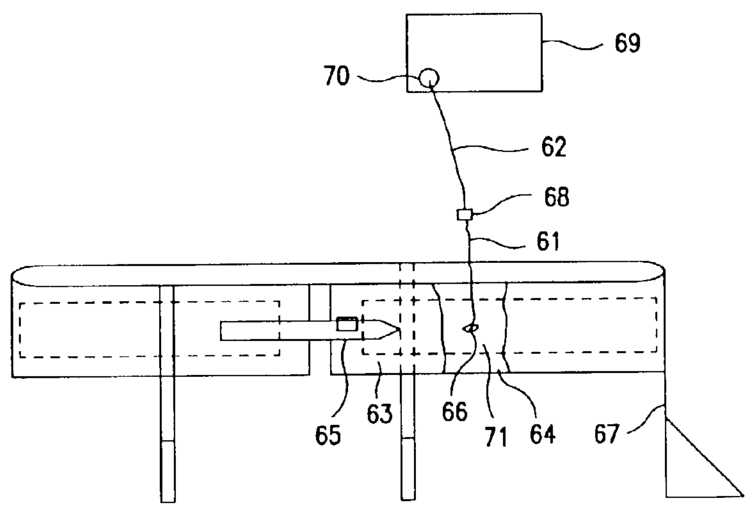
FIG. 3 shows a more detailed view of the foil and its supports, and further shows connection of the foil to a computer.

The foil belt transducer, as more fully shown in FIG. 3, consists of a metallic strip 71 of aluminum or copper or other conductive metallic material covered with two insulation members 63 and 64 that cover the foil 71 on both sides and ends. A strap and buckle 65, attached to the ends of the belt, secures the transducer belt around the pile and permits the belt to be arranged about or removed from about the pile at any time. Although a strap and buckle are shown as the releasable connecting means, other types of releasable connectors could be employed. As seen in FIG. 3, the ends of the foil 71 do not overlap; therefore, no capacitance is formed between the ends of the foil. To elevate the belt assembly up away from the mud and water that generally exists on a job site, supports 67, positioned on the ground adjacent the pile, are fastened to the belt insulation members 63 and 64 and support the belt in a noncontact relationship with the pile. The foil sensor does not require physical contact with the pile for measurement. A single conductor cable 61 is fastened to foil at 66 and is run to a connector 68. From connector 68 a single conductor cable 62 leads to a computer 69 via terminal 70. The computer 69 is equipped with a Labview program which when activated by a blow of the hammer yields a curve similar to that shown at FIG. 5. As noted above, although a single conductor cable 61 connected to one end of the foil is shown in FIG. 3, a dual conductor cable could also be used. In the latter case the second conductor would be connected to the other end of the foil. The two conductors would then be connected to the computer to display the sensed signal.

Alternatively, the computer could be replaced with an oscilloscope or a chart recorder to display the sensed signal.

Figure 4:
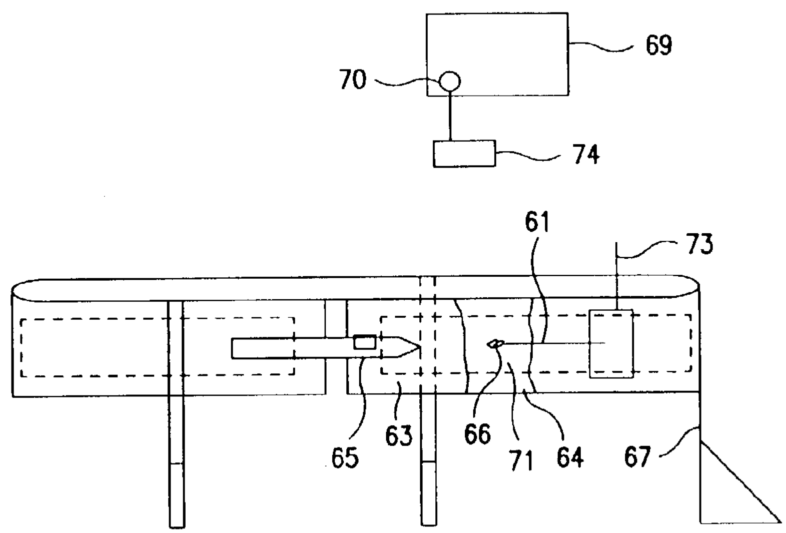
FIG. 4 shows an alternative connection of the foil to a computer.
Figure 5:
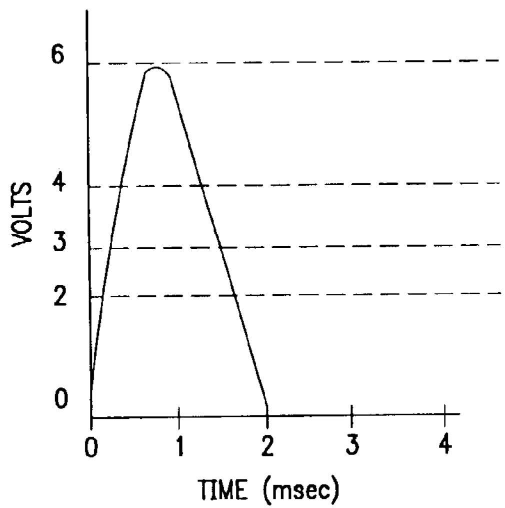
FIG. 5 is a graph showing the volts sensed verses the time of sensing.

Besides a direct cable conductor 61 to the computer 69, as shown in FIG. 3, a wireless system can be employed as shown in FIG. 4. This system consists of a small transmitter 73 mounted in a pouch 72. Conductor cable 61 is connected to the transmitter or the two conductors are connected to the transmitter if the dual conductor embodiment is used. Since the signal, as represented in the curve of FIG. 5 is analogue, it is essential that the transmitter incorporate a converter that will convert analogue signals to digital signals. This information can be carried on the same frequencies and equipment that is in use today by cellular phones. The receiver 74 at the computer will need to be equipped with an inverter (digital analog converter) to get the signals back to analogue. The advantage of this arrangement is that it eliminates the need for a long cable to connect the transmitter to the receiver, and the problems associated with such a cable. Also, this allows the computer and technician to be in an office some distance from the actual pile driving job.

Still another way would be to connect cable 61 or the alternative dual conductor cable from the foil belt to a telephone line through a converter. While not shown, such an arrangement could easily be accomplished.

Figure 6:
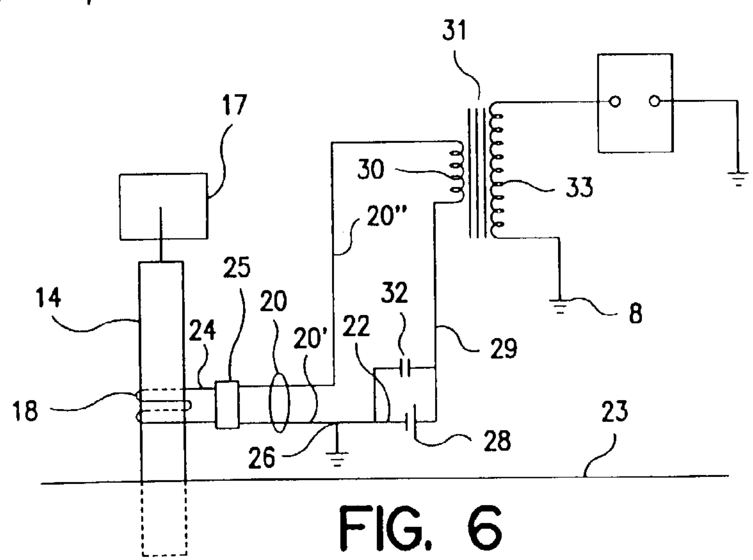
FIG. 6 shows a view of a prior art system using the transducer and readout system, and having an impedance matching transformer.

With previous sensor systems, as illustrated in prior art FIG. 6, since the transducer is positioned substantially at ground level, it could be situated prior to erecting the pile into place, but then the lower end of the pile had to be lifted up over the sensor and then positioned within sensor. Alternatively, the sensor could be lifted up over the top of the pile after the driving operation had started, and therefore the cable needed to be sufficiently long to accomplish this purpose, or the cable could be provided with some type of disconnect means.

In prior art FIG. 6, there is shown a pile 14 which has been partially driven into the earth 23 by means of the pile driving hammer 17 shown supported above it. Loosely wound around pile 14 is the transducer 18, which comprises a single conductor 24, both ends of which terminate in a connector means 25. Extending from the connector means 25 and electrically connected to the transducer 18 is a pair of conductor cables 20 with one wire 20' being connected to ground at point 26. Also connected to ground at point 26 by a wire 22 is the negative terminal of battery 28 with the positive terminal connected by wire 29 to one end of the primary winding 30 of impedance matching transformer 31.

It will be clear to those skilled in the art that a signal is induced into the transducer 18 by the magnetic field produced in the steel pile when it is struck and that this signal bypasses the battery through the capacitor 32 and is then amplified by the transformer action in the impedance matching transformer 31 to a usable voltage level to drive the oscilloscope 37. The signal level is proportional to the force with which the pile is struck and therefore the amplitude of the signal displayed on the oscilloscope is also proportional to the force.

The invention provides a means to determine the safe bearing capacity of a pile by knowing the ultimate bearing achieved by a pile hammer capacity.

The invention provides a means to determine the hammer size, as opposed to one that is too small or too large, through the use of the impact curve.

The invention contemplates the use of a computer to obtain the impact curve to monitor the system.

I claim:

1. A foil belt sensor, for use in a pile driving system to determine the driving force applied to the pile by the pile driving system, which foil belt sensor is capable of being wrapped and unwrapped about a pile comprising, a flexible metallic sheet surrounded on both sides and ends by insulating means; releasable connection means, connected to the insulation at each end of the sheet and extending longitudinally away from the ends, for releasable connection to one another for permitting the insulated metallic sheet to be assembled and disassembled around the pile, wherein, when the flexible metallic sheet is assembled around the pile, the flexible metallic sheet senses the change in voltage versus time that is generated in a pile by the sudden impact against the pile by the pile driving system.

2. The foil belt sensor of claim 1, wherein, when the releasable connection means are connected to one another to assemble the insulated metallic sheet around the pile, the ends of the metallic sheet are spaced apart and do not overlap.

3. The foil belt sensor of claim 1, wherein the metallic sheet is aluminum or copper or other conductive metallic material.

4. The foil belt sensor of claim 1, wherein the releasable connecting means comprises a buckle and strap.

5. The foil belt sensor of claim 1, further including a wireless connection from the sensor to a recording means.

6. The foil belt sensor of claim 5, wherein the wireless connection includes a transmitter mounted on the sensor and a receiver mounted some distance away.

7. The foil belt sensor of claim 6, wherein the transmitter includes an analogue to digital converter, and the receiver includes a digital to analogue converter.

8. The foil belt sensor of claim 6, wherein the insulating means includes a pocket which holds the transmitter.

9. A foil belt sensor, for use in a pile driving system to determine the driving force applied to the pile by the pile driving system, which foil belt sensor is capable of being wrapped and unwrapped about a pile comprising, a flexible metallic sheet surrounded on both sides and ends by insulating means; releasable connection means, connected to the insulation at each end of the sheet and extending longitudinally away from the ends, for releasable connection to one another for permitting the insulated metallic sheet to be assembled and disassembled around the pile, wherein, when the flexible metallic sheet is assembled around the pile, the flexible metallic sheet generates an output which is indicative of the driving force that is generated in a pile by the sudden impact against the pile by the pile driving system.

10. The foil belt sensor of claim 9, wherein, when the releasable connection means are connected to one another to assemble the insulated metallic sheet around the pile, the ends of the metallic sheet are spaced apart and do not overlap.

11. The foil belt sensor of claim 9, wherein the metallic sheet is aluminum or copper or other conductive metallic material.

12. The foil belt sensor of claim 9, wherein the releasable connecting means comprises a buckle and strap.

13. The foil belt sensor of claim 9, further including a wireless connection from the sensor to a recording means.

14. The foil belt sensor of claim 13, wherein the wireless connection includes a transmitter mounted on the sensor and a receiver mounted some distance away.

15. The foil belt sensor of claim 14, wherein the transmitter includes an analogue to digital converter, and the receiver includes a digital to analogue converter.

16. The foil belt sensor of claim 14, wherein the insulating means includes a pocket which holds the transmitter.

* * * * *